US011116864B2

(12) United States Patent
Anderson et al.

(10) Patent No.: US 11,116,864 B2
(45) Date of Patent: Sep. 14, 2021

(54) DEVICES AND METHODS FOR PROTECTING AND OFFLOADING PRESSURE IN CASTING NEUROPATHIC AND DIABETIC WOUNDS OF THE FOOT

(71) Applicant: WoundKair Concepts, Inc., Benbrook, TX (US)

(72) Inventors: Danny E. Anderson, Aledo, TX (US); Kimberly G. Anderson, Aledo, TX (US)

(73) Assignee: Woundkair Concepts, Inc., Forth Worth, TX (US)

(*) Notice: Subject to any disclaimer, the term of this patent is extended or adjusted under 35 U.S.C. 154(b) by 299 days.

(21) Appl. No.: 16/439,940

(22) Filed: Jun. 13, 2019

(65) Prior Publication Data
US 2020/0009287 A1  Jan. 9, 2020

Related U.S. Application Data

(60) Provisional application No. 62/695,494, filed on Jul. 9, 2018.

(51) Int. Cl.
| | |
|---|---|
| *A61F 5/00* | (2006.01) |
| *A61L 15/14* | (2006.01) |
| *A61L 15/12* | (2006.01) |
| *A61F 13/06* | (2006.01) |
| *A61F 5/01* | (2006.01) |

(52) U.S. Cl.
CPC ............ *A61L 15/14* (2013.01); *A61F 5/0111* (2013.01); *A61F 13/066* (2013.01); *A61L 15/12* (2013.01)

(58) Field of Classification Search
None
See application file for complete search history.

(56) References Cited

U.S. PATENT DOCUMENTS

| | | | |
|---|---|---|---|
| 4,946,726 A | 8/1990 | Sandvig et al. | |
| 4,947,838 A | 8/1990 | Giannetti | |
| 5,584,799 A | 12/1996 | Gray | |
| 5,735,805 A | 4/1998 | Wasserman et al. | |
| 5,913,840 A | 6/1999 | Allenberg et al. | |
| 6,334,854 B1 | 1/2002 | Davis | |
| 6,595,937 B1 | 7/2003 | Moon et al. | |
| 8,100,843 B2 | 1/2012 | Rousseau et al. | |
| 8,303,527 B2 | 11/2012 | Joseph | |
| 9,839,548 B2 | 12/2017 | Ingvarsson et al. | |
| 2011/0264022 A1 | 10/2011 | Freeman et al. | |
| 2013/0035620 A1 | 2/2013 | Schutz et al. | |

(Continued)

*Primary Examiner* — Kim M Lewis
(74) *Attorney, Agent, or Firm* — Whitaker Chalk Swindle & Schwartz; Charles D. Gunter, Jr.

(57) ABSTRACT

A method and device are shown for use in casting for Total Contact Casting for offloading pressure in neuropathic and diabetic wounds or fractures of the appendages such as the human leg or foot. The outer casting material used can be comprised of traditional casting materials. A total foot protection pad underlies the traditional casting materials. It is a one piece moldable system that encompasses the total foot from the Achilles along the lateral and medial foot, covering the plantar surface, the malleoli and folds and extends over the dorsum. The one piece system has adhesive backing on a contact side to facilitate its application and/or forms a total foot protection pad beneath the outer hardened casting material.

7 Claims, 7 Drawing Sheets

(56) References Cited

U.S. PATENT DOCUMENTS

| | | | |
|---|---|---|---|
| 2014/0316316 A1* | 10/2014 | Andrews | A61F 13/04 |
| | | | 602/12 |
| 2015/0005684 A1 | 1/2015 | Evans | |
| 2015/0025429 A1 | 1/2015 | Liden et al. | |
| 2015/0025432 A1* | 1/2015 | Liden | A61F 5/0585 |
| | | | 602/12 |
| 2017/0105863 A1 | 4/2017 | Anderson et al. | |
| 2017/0239097 A1* | 8/2017 | Serena | A61F 5/0111 |

* cited by examiner

DEVICES AND METHODS FOR PROTECTING AND OFFLOADING PRESSURE IN CASTING NEUROPATHIC AND DIABETIC WOUNDS OF THE FOOT

CROSS REFERENCE TO RELATED APPLICATION

The present application claims priority to U.S. Provisional Patent Application Ser. No. 62/695,494 filed Jul. 9, 2018, by the same inventors and with the same title.

BACKGROUND OF THE INVENTION

Field of the Invention

The present invention relates generally to orthopedic bandages, splints, and casts and more particularly to casting techniques for both orthopedic and total contact casting for offloading pressure in neuropathic and diabetic wounds or fractures of the human appendages, such as the foot or leg.

Description of the Prior Art

An orthopedic cast, body cast, plaster cast, or surgical cast, is a shell, frequently made from plaster or fiberglass, encasing a limb (or, in some cases, large portions of the body) to stabilize and hold anatomical structures, most often a broken bone (or bones), in place until healing is achieved. Orthopedic casts made of Plaster of Paris have a long history of use because of their ability to immobilize a broken bone or other portion or appendage of a body while healing takes place. Plaster of Paris casts are formed using a fabric tape such as cotton muslin that is impregnated with a solution of calcium sulfate. The cast hardens as the material dries, forming a rigid shell around the site of the injury. A more recent substitute for the Plaster of Paris is the use of fiberglass tape impregnated with a synthetic resin. A fiberglass cast is also an effective immobilizer, is lighter than a plaster cast, and takes less time to apply and harden.

A specialized type of cast, referred to herein as a "full contact cast" or "Total Contact Cast" (TCC) is a specially designed cast designed to take weight off the foot (offloading) and is particularly useful in treating patients with diabetic foot ulcers (DFUs). Reducing pressure on the wound by taking weight of the foot has proven to be very effective in DFU treatment. DFUs are a major factor leading to lower leg amputations among the diabetic population in the United States. TCC has been used for off-loading DFUs in the United States since the mid-1960s and is regarded by many practitioners as the "reference standard" for offloading the bottom surface of the foot.

TCC involves encasing the patient's complete foot, including toes, and the lower leg in a special type of cast that redistributes weight and pressure in the lower leg and foot during everyday movements. As with orthopedic casts in general, materials used in applying the TCC have changed over the years, from the use of unmodified Plaster of Paris, to formulations containing fiberglass and other materials.

While effective for their particular intended purposes, both of these traditional types of cast construction have certain disadvantages. They are sometimes heavy and they are often not fully conformable. The traditional cast typically leaves voids within its hardened shell, which prevents the cast from providing uniform, full-contact support. The lack of uniform support can lead to inflammation, abrasions, dermatitis, ulceration, and even infection, depending on the type injury requiring the application of a cast to immobilize the patient's limb, foot, etc.

In the case of the Total Contact Cast, while important in the treatment and post-treatment of wounds or fractures and aiding in the fractures healing process, pressures need to be redistributed throughout both the bottom of the cast and the cast wall in order to reduce pressures to the wound's or fracture's site. Many times a TCC does not address foot deformities, arches, and other voids that the cast or cast application does not address. A TCC should be in contact with the entire foot and lower leg in order to properly offload the wound or fracture. Many times, the traditional cast is supported by a boot or a shoe. Evidence has been documented that removable support devices such as a boot or a shoe are only worn 28% of the steps taken by a patient wearing these devices.

Often times a traditional wrapped Total Contact Cast can be applied with too much or too little pressure, causing secondary ulcerations and/or discomfort from pressure or from moving or shifting while being worn. The use of simple rolls of cast padding allows for rubbing on bony prominences and leaves room for error. Many physicians today refuse to cast because of problems associated with secondary ulceration due to rubbing which has led to amputation of a diabetic limb in some cases.

Thus, despite the advances which have been made in casts of the type under consideration, there exists a need for improvements in casting so that the entire foot is surrounded by a protective pad and therefore there are no areas that will have too much or too little pressure and no area of the foot may rub itself while in the cast.

A need exists for a simple and economical method for casting using unique casting techniques which reduce the possibility of errors of the type discussed and which reduce the risk of having an ulcer being rubbed on the leg, heel, ankle or toes of the patient.

A need exists for such an improved casting technique which can be applied in one quick application using relatively inexpensive and readily available materials.

SUMMARY OF THE INVENTION

The present invention relates to casting both Orthopedic and Total Contact Casting for offloading pressure in neuropathic and diabetic wounds or fractures of the appendages such as a leg or a foot. The outer cast system itself is comprised of traditional casting materials. The improved casting method described herein uses a total foot protection pad which underlies the traditional hardened casting material. The total foot protection pad is a one piece moldable system that encompasses the total foot from the plantar surface and hind foot (Achilles), over the malleoli and continuing along the lateral and medial foot, the material continuing to fold over the dorsum of the foot. This one piece pad has adhesive backing on the contact side to make it easy and quick to apply.

It is an objective of the present invention to provide an effective protection for the entire foot while its rests inside the traditional cast materials. The present invention also protects the foot from casts that are applied either incorrectly, with too much pressure, or too little pressure. As has been discussed, if a cast is applied incorrectly with traditional pre-cast supplies there is very high likelihood that the cast will rub a sore into the patient's foot or leg and also possibly cause secondary ulcerations due to too much pressure being applied.

In one form of the invention, an article is provided which is suitable for use in forming a Total Contact Cast around the foot and leg of a human patient. The article is formed from a unitary blank having a top contact surface and an opposite bottom surface and having major and minor generally rectangular planar regions separated by opposing flap regions. The major rectangular planar region is sized to receive a plantar surface of the human foot with the minor rectangular planar region being sized to receive a hind foot region of the human foot. The opposing flap regions are selectively sized to cover opposing ankle regions (malleoli) of the human foot. The rectangular planar regions and flap regions are formed of a pliable foam material so as to be foldable to encompass and envelope the entire foot. Preferably, the pliable foam material is an open-celled polyurethane foam material. The top, contact region of the unitary blank preferably has an adhesive applied thereto for restraining the unitary blank about the foot upon folding of the blank. The unitary blank can also have a plurality of holes formed therein which communicate the top contact surface and the opposite bottom surface.

The article of the invention, as described, is used in making an improved Total Contact Cast for a human foot and leg. A cured, outer casting material is used in traditional fashion to form a hardened cast which surrounds the foot and a portion of the leg. However, in forming the cast of the invention, a novel padding material, as previously described with respect to the article of the invention, is applied to the foot and leg prior to curing the outer casting material so as to underlie the outer casting material. The padding material comprises the previously described a unitary blank.

A novel method is also shown for forming an improved total contact cast around a foot and leg region of a human patient, the method comprising the steps of:

providing a unitary blank having a top contact surface and an opposite bottom surface and having major and minor generally rectangular planar regions separated by opposing flap regions, the major rectangular planar region being sized to receive a plantar surface of the human foot with the minor rectangular planar region being sized to receive a hind foot region of the human foot, the opposing flap regions being sized to cover opposing ankle regions of the human foot, the rectangular planar regions and flap regions being formed of a pliable foam material so as to be foldable to encompass and envelope the entire foot;

placing the patient's plantar foot region onto the top planar surface of the unitary blank;

folding up the minor rectangular planar region of the unitary blank so as to cover the patient's hind foot region;

folding up the opposing ankle regions of the unitary blank to cover the patient's ankle regions;

folding back the major rectangular planar region of the unitary blank to cover the patient's dorsal foot region and thereby form a total foot protection pad;

applying a curable casting material about the total foot protection pad and foot and leg region of the patient and allowing the casting material to cure to form a hardened cast.

Additional object, features and advantages will be apparent in the written description which follows.

DETAILED DESCRIPTION OF THE INVENTION

The present invention may be understood more readily by reference to the following detailed description of the preferred embodiments of the invention. However, before the casting system and methods are disclosed and described, it is to be understood that this invention is not limited to specific cast types, assemblies or configurations, specific conditions, or specific methods, as such may vary, and any modifications thereto and variations therein will be apparent to those skilled in the art. It is also to be understood that the terminology used herein is for the purpose of describing specific embodiments only and is not intended to be limiting.

As discussed in the Background of the invention, the present invention may be used generally in the field of orthopedic casts and has particular applicability to Total Contact Casting techniques of the type used for offloading wounds or fractures often encountered by diabetic and neuropathic patients. As has been briefly discussed, a Total Contact Cast is placed on a patient's foot and leg region in order to redistribute plantar pressure and to address other types of issues like shearing and shocking forces that cause breakdown or cease healing of the wounds or fractures. These types of casts are also used to alter the patients' gait to keep pressures equal through the pedal wounds or fractures.

In the discussion which follows, the term Total Contact Cast will thus be taken to mean that the body of the cast is in full and even conformance with the surface of the encased body part, providing maximum support and uniform distribution of forces and pressures that act on the encased limb, while minimizing any voids inside the cast structure that impair the uniform distribution of pressure to the encased limb. For example, most advantageously, the Total Contact Cast is installed on a person's foot, ankle, and lower leg—a "short leg cast," which will adapt to many contours due to the shape of the foot, its arch and ankle, with any deformities that may be present in an individual, and the like being accommodated, without exerting undue pressure upon any portion of the encased part, particularly any surface wound inside the cast.

The use of a Total Contact Cast is advantageous in the treatment and post treatment of wounds or fractures of the type previously described with respect to diabetic and neuropathic patients in contributing to and facilitating the healing process. In these situations, pressures need to be redistributed throughout both the bottom of the cast and the cast wall in order to reduce pressures to the wound or fracture site. Nevertheless, there are many times in which a Total Contact Cast fails to adequately address foot deformities, arches, and other voids that the traditional casting process fails to accommodate.

A properly applied Total Contact Cast should be in contact with the entire foot and lower leg in order to properly offload the wound or fracture. Devices being utilized in this space at the present time include both traditional and roll on casts usually supported by a boot or a shoe. As mentioned, evidence has been documented that removable support devices such as a boot or a shoe are only worn 28% of the steps taken by a patient wearing these devices. Also, the traditionally wrapped Total Contact Cast can be applied with too much or too little pressure, causing secondary ulcerations and/or discomfort from pressure or from moving or shifting while being worn. With the use of the present invention, the entire foot is surrounded by a Total Foot Protection Pad and therefore there are no areas that will have too much or too little pressure and no area of the foot may rub itself while in the cast.

As used herein, "lower leg" may refer to any portion of a patient's leg that is located distal to the patient's knee and including the patient's foot.

As used herein, the terms "patient" and "individual" refer to any person or other subject that can wear or use the described cast system. In certain embodiments, the patient is a person suffering from a diabetic or neuropathic ulceration, sore, or other type of wound in an appendage (e.g., lower leg).

As will be well understood by those skilled in the relevant arts, traditional casting techniques use a hardenable casting material which may be configured so as to extend over a first surface of a patient's appendage (e.g., lower leg), and over the entire foot region. For example, the cast may be configured so as to extend: over a posterior portion of a patient's lower leg (e.g., calf), over the patient's heel, across a length of the sole of the patient's foot, over an anterior portion of the foot (e.g., toes), across a dorsal portion of the foot; and over an anterior portion of the lower leg (e.g., shin). In accordance with typical practice, the patient's foot and leg are first typically covered with a stockinette. Fabric padding material would then be applied over the stockinette. A system of felt strips would then be applied to the outside of the stockinette to provide structural form to the finished cast. Next, the hardenable cast material would be applied and cured. If the patient has wounds or sores, these would be dressed prior to applying the stockinette.

Figure 1:
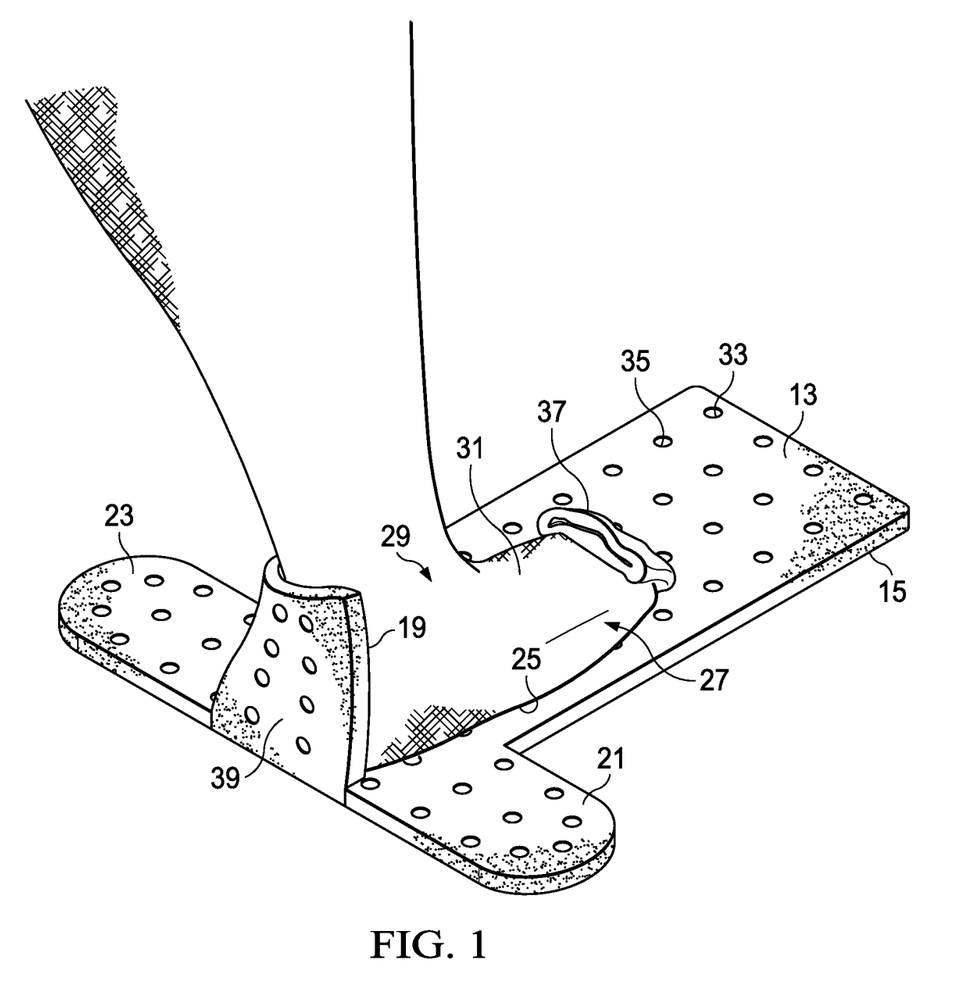
FIG. 1 illustrates a lower leg of a patient with a stockinette applied, with the patient's foot resting on the protective pad used in the method of the invention where a portion of the pad covers the hind foot region (Achilles)
Figure 5:
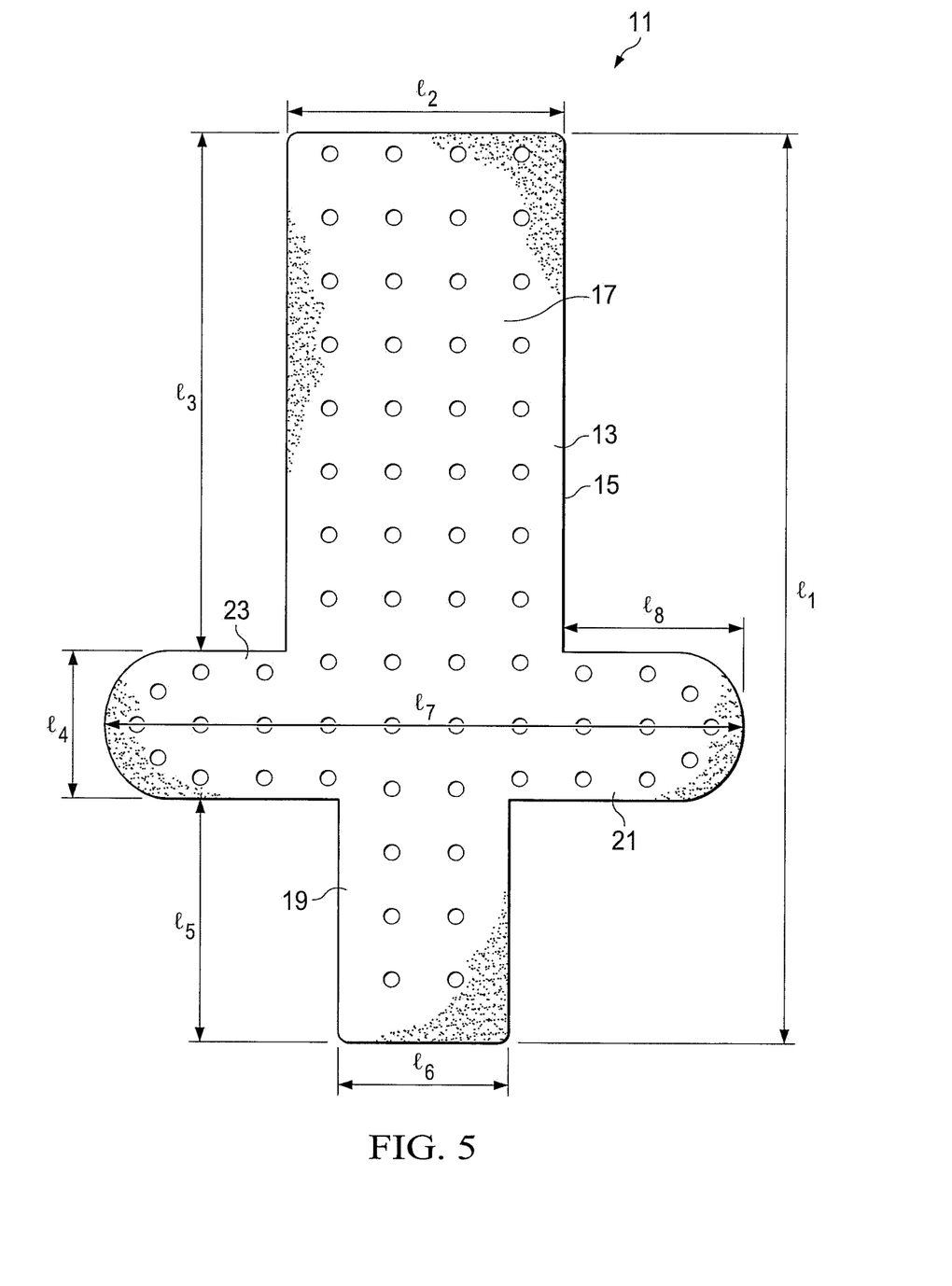
FIG. 5 if a top planar view of the protective pad of the invention in the relaxed state prior to application to a patient's foot.

The Inner Total Foot Protection Pad:

The techniques and devices used in the practice of the method of the present invention utilize a novel unitary blank or pad shown in isolated fashion in FIG. 5 of the drawings. The novel blank, designated generally as 11. The blank 11 has a top contact surface 13, an opposite bottom surface 15 and has major and minor generally rectangular planar regions 17, 19, which are separated by opposing flap regions 21, 23. The major rectangular planar region 17, as will be appreciated from FIG. 1, is selectively sized to receive a plantar (bottom) surface 25 of the human foot 27. The minor rectangular planar region 19 (FIG. 1) is sized to receive a hind foot region (sole or Achilles) of the human foot. The opposing flap regions 21, 23, are appropriately sized to cover opposing ankle regions (such as region 29 in FIG. 1) of the human foot.

Figure 4:
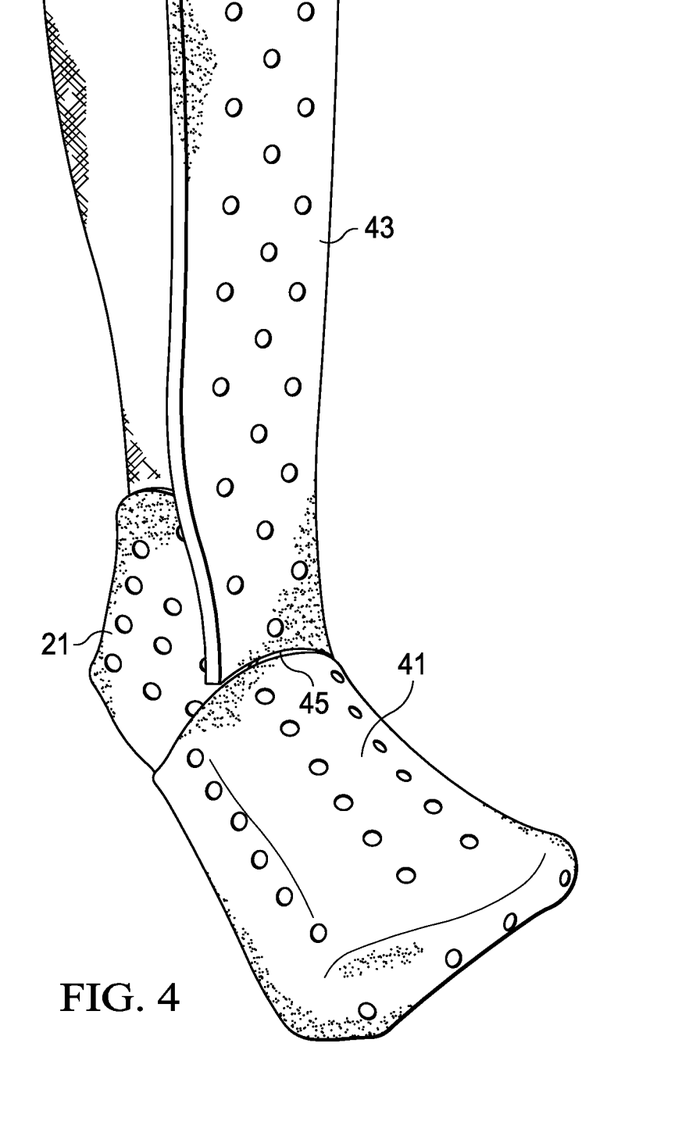
FIG. 4 illustrates the final step of preparing the patient's foot for the casting operation in which a longitudinal strip of foam padding is applied to the patient's leg.

The rectangular planar regions 17, 19, and flap regions 21, 23, are preferably formed in a single piece of a pliable foam material so as to be foldable to encompass and envelope the entire foot, as best seen in FIG. 4. While a number of suitable materials might be utilized for the manufacture of the unitary blank 11, one particularly preferred material is an open-celled polyurethane foam material. In one case, an 180-90 Flexible Polyurethane Foam was utilized. The polyurethane foam which was used was commercially available and was manufactured using known manufacturing techniques.

The polyurethane foam blank 11 had a pressure sensitive adhesive applied to the upper, contact surface (generally the whole upper surfaces made up of the regions 17, 19, 21 and 23 in FIG. 5). The pressure sensitive adhesive is applied to the upper surfaces of the unitary blank prior to the blank being die cut to form the finished pad shown in FIG. 5. The pressure sensitive adhesive is used to restrain the unitary blank about the patient's foot in use, as will be further described. The typical pad shown in FIGS. 1 and 5 is approximately ⅜ inch thick. While the ultimate dimensions of the finished pad might vary somewhat depending upon the age and size of the patient, exemplary dimensions for the pad shown in FIG. 5 are as follows:

$L1$=22 inches
$L2$=7 inches
$L3$=14 inches
$L4$=4 inches
$L5$=4 inches
$L6$=3 inches
$L7$=15 inches
$L8$=4 inches While these dimensions are exemplary, it will be appreciated that the unitary blank (see FIG. 1) is generally longitudinally dimensioned in a first direction to extend past the foot a sufficient length to be foldable back to provide an overlap region over a dorsal surface (generally at 31) of the foot. In similar fashion, the opposing flap regions 21, 23, of the unitary blank have an outer curvilinear shape defining outwardly extending projections. The projections are positioned and dimensioned to be formed around opposing ankle regions 29 of the foot to form a substantially smooth and pucker five enclosure (see FIGS. 2 and 3). The unitary blank 11 also preferably has a plurality of holes (such as holes 33, 35 in FIG. 1) formed therein which communicate the top contact surface 13 and the opposite bottom surface 15.

FIGS. 1-4 of the drawings show the steps involved in applying the unitary blank 11 to the foot, ankle and lower leg region of a human patient. As shown in FIG. 1, after any wounds or sores on the foot have been treated, it is typically wrapped in a cloth sockinette 37 and the bottom, plantar surface of the foot is placed on the top surface 13 of the blank. The heel portion 39 can then be folded up over the patient's heel region. The pressure sensitive adhesive helps to hold the heel portion of the flexible pad in the position shown in FIG. 1.

Figure 2:
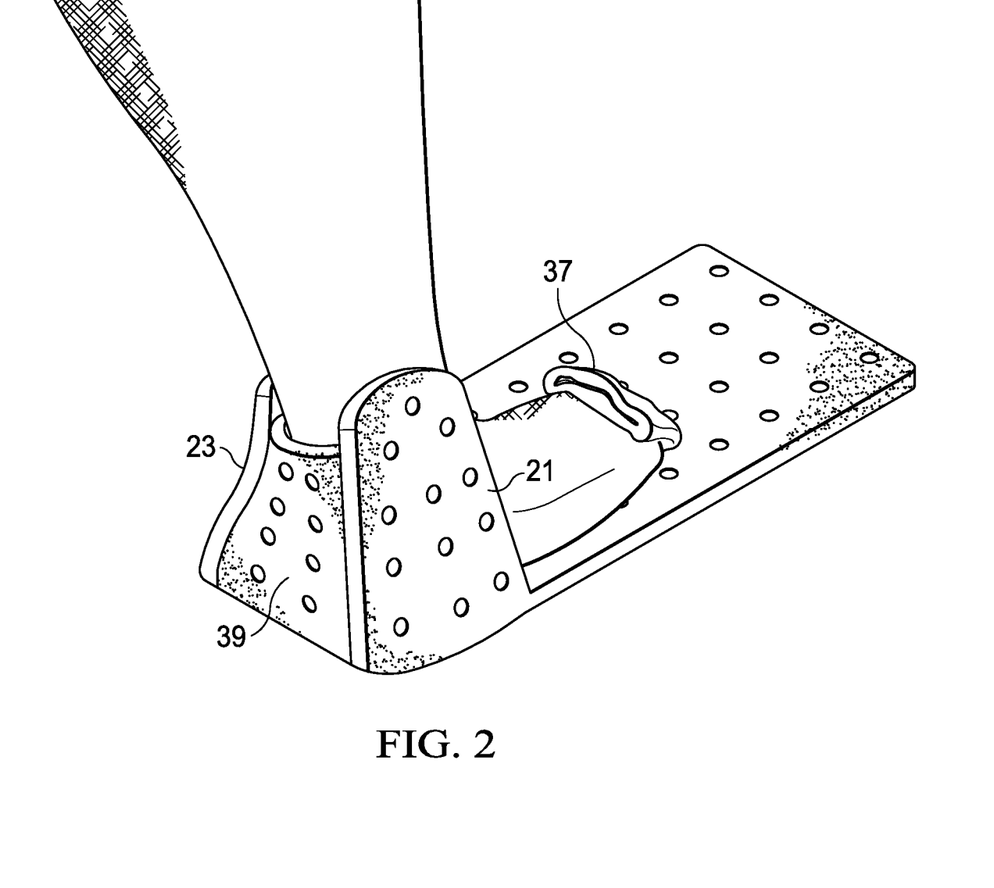
FIG. 2 is a view similar to FIG. 1, but showing the next step in applying the total protection pad to a patient's foot where the side flaps of the pad cover the patient's ankle regions.
Figure 3:
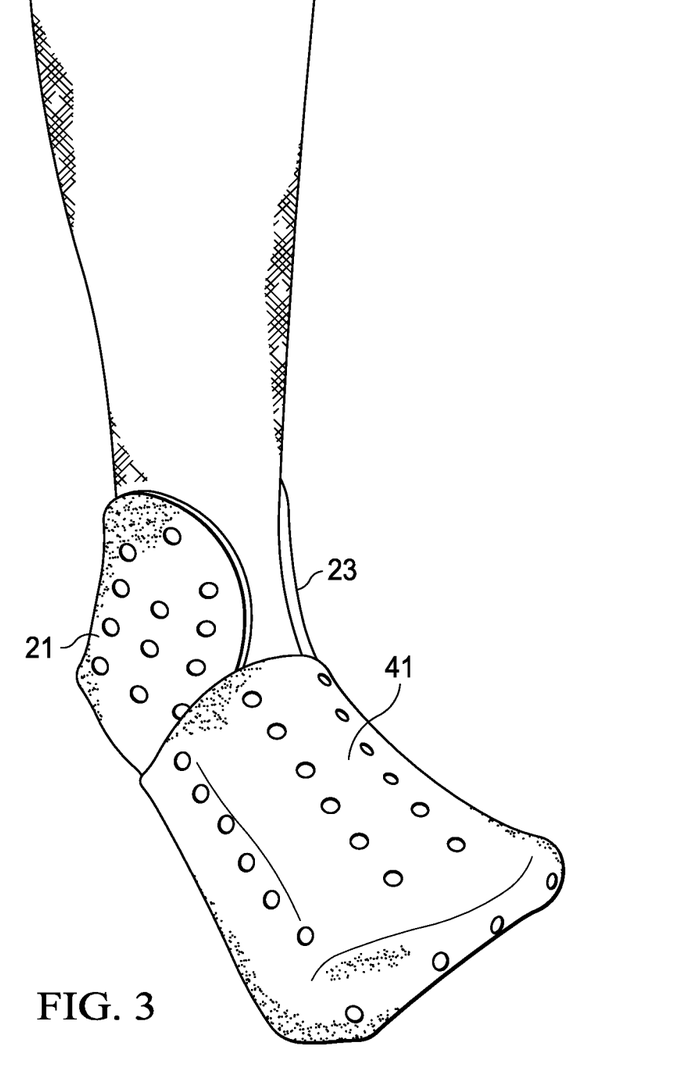
FIG. 3 shows the continuation of the application of the protective pad of the invention to the patient's foot, with the pad covering the foot dorsum region.

As shown in FIGS. 2 and 3, the opposing flaps 21, 23, are then folded over the ankle regions of the patient. Next, as shown in FIG. 3, the front planar region 41 of the pad is folded back over the dorsal (top) region of the foot. Again, the pressure sensitive adhesive helps in keeping the flexible pad in the desired position shown in FIG. 3.

In most cases, a longitudinal strip of padding material (43 in FIG. 4) is then placed down the front of the patient's leg, running down the lower leg region to the outer edge 45 of the front planar region of the folded pad. The longitudinal strip 43 shown in FIG. 4 is approximately 3 inches×18 inches in dimension, and can be easily cut to size, if necessary. It can be formed of the same material as the unitary blank previously described.

Figure 6:
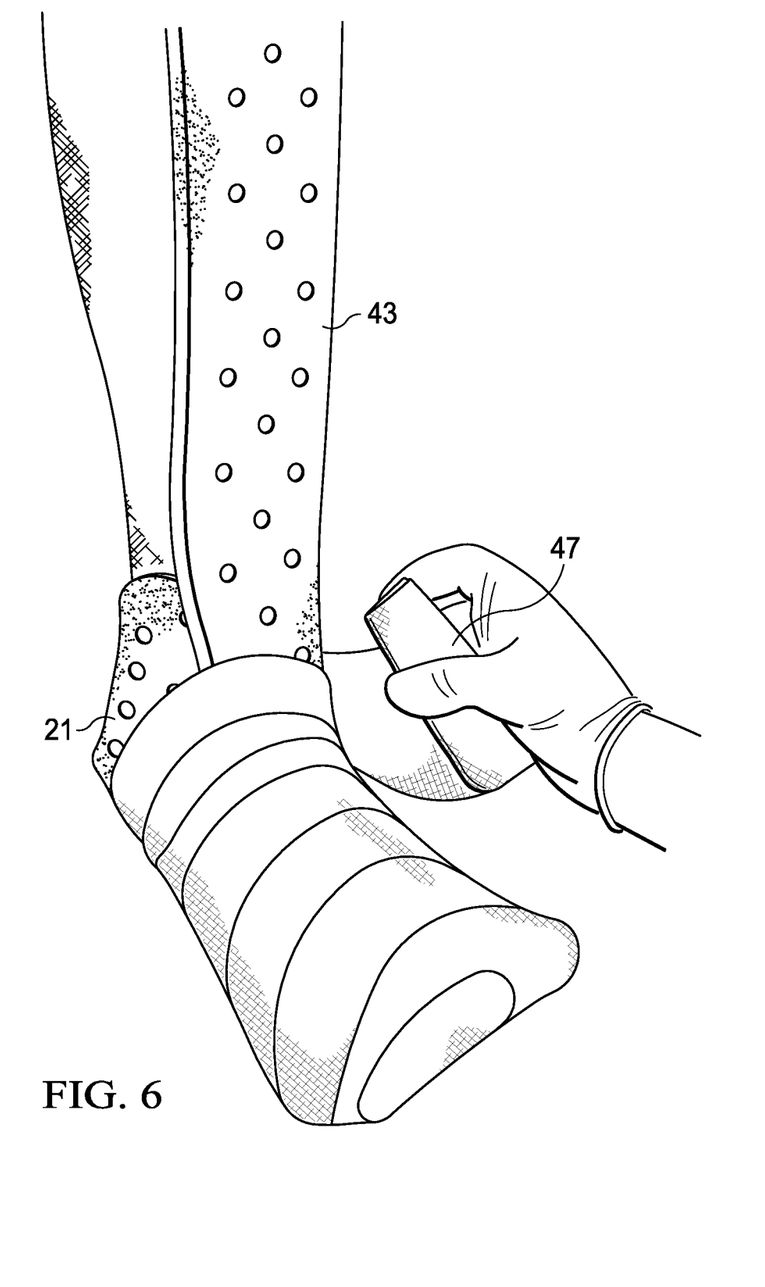
FIGS. 6 and 7 of the drawings show a traditional casting material being applied to the patient's foot and leg to cover the protective pad of the invention.
Figure 7:
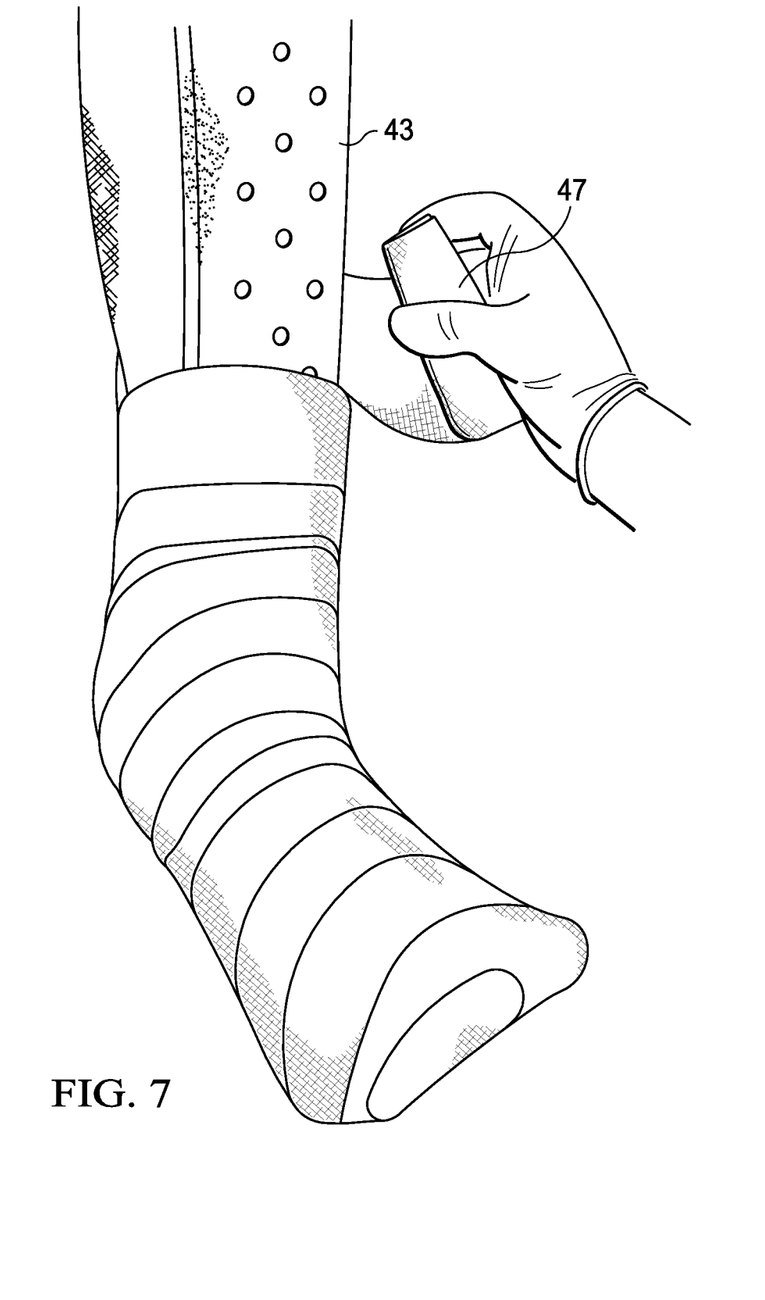

A "traditional" casting material is then typically applied over the flexible pad. FIGS. 6 and 7 show the beginning steps in wrapping the folded pad with a cast tape 47. The traditional casting material can take any number of a variety of known forms which will be familiar to those in the relevant industry. It will generally be a casting material which is configured to harden around the padding layer and form an outer shell of the cast surrounding the patient's limb. Various components of the traditional casting systems to be described can be used in any suitable manner that allows the components (individually or in combination) to help protect a wounded portion of a patient's limb. The casting material will generally be a hardening material selected from the group consisting of fiberglass, carbon fiber, thermoplastic, bandaging, casting tape, coated fabrics, and combinations thereof. In certain embodiments, the casting material is configure to begin hardening and form the outer shell upon exposure to air and/or water or to U/V light.

The various components of the traditional cast system can be used in any suitable combination, meaning that portions of the cast system can be omitted and/or replaced with one or more known or novel components, and any additional components (such as, e.g., wound dressing, casting material, boot, footplate, shoe, ointment, etc.) can be added or used with one or more components of the described cast system.

The Outer Traditional Casting Material:

The outer traditional casting materials described herein can comprise any suitable casting material that allows the cast to substantially conform to the shape of a patient's appendage (e.g., lower leg) during application and then harden in that shape to form a rigid cast. Examples of suitable casting materials include (but are not limited to) any known or novel: fiberglass casting material (e.g., fiberglass that has been impregnated with polyurethane and/or another suitable material, fiberglass that is coated with and/or otherwise comprises silver, copper, nickel, iodine, bamboo, and/or another suitable antimicrobial material and/or anti-odor material, and/or combinations thereof); hardenable bandaging (e.g., cotton bandaging that is coated with plaster, polyester bandaging that is covered with plaster, and/or any other suitable bandaging material that is configured to harden after application); a thermoplastic casting material; a polypropylene casting material; a carbon fiber casting material; a hardenable antimicrobial material, such as, e.g., a plaster or another suitable hardenable material covering a bamboo cloth, a bamboo rayon, a polyester made from bamboo, other types of fabric comprising bamboo, and/or a silver-coated fabric (e.g., silver coated polyethylene terephthalate, sliver-coated rayon, silver-coated polyester, etc.), a copper coated fabric, a silver/copper-coated fabric, a silver/copper/nickel-coated fabric, a silver/copper/tin-coated fabric, an iodine incorporated, cloth, and/or any other suitable material having one or more antimicrobial and/or anti-odor features; a casting material (e.g., fiberglass, cotton bandaging, and/or any other suitable casting material) that is impregnated with and/or otherwise comprises a suitable antibiotic, bactericide, and/or other antimicrobial ingredient (e.g., penicillin, amikacin gentamicin, kanamycin, netimicin, tobramycin, streptomycin, spectinomycin, geldanamycin, herbimycin, rifaximin, ertapenem, doripenem, imipenem, meropenem, defadroxil, cefazolin, cefalotin, cephalexin, and/or any other suitable antimicrobial); casting tape; and/or any other suitable material that is configured to be formed around a portion of a patient's limb and then hardened to form a rigid cast. In one preferred form, the outer shell is a fiberglass material that begins hardening once it is exposed to air and/or water.

As has been briefly described, the cast can comprise any suitable number of layers of casting material. For example, the cast of the invention may comprise between 1 and 20 layers of casting material, including any suitable number of layers of casting material that fall within the aforementioned range, such as, e.g., between 5 and 10 layers. The casting material can also have any suitable thickness, such as between 1 mm and about 4 cm.

The casting material may be in the form of a plurality of strips or a single strip configured to form an outer shell of the cast on an appendage (e.g., lower leg). The strips can have any suitable shape, such as, e.g., rectangular, belt-shaped, triangular, rounded, polygonal, irregular, symmetrical, asymmetrical, ribbon-like, cord-like, rope-like, and/or any other suitable shape. The casting material may furthermore be of any desired length or lengths (if a plurality of strips, are to be applied) to form an outer shell of the cast of the desired thickness and covering the desired body part. For example, some of the strips may be configured to circumscribe a portion of the cast, some of the strips may be configured to extend only partially around a part of the cast, or some of the strips may be configured to overlap with each other. While the strips can run substantially perpendicular to a length (or a longitudinal axis) of the cast, the straps may also, or alternatively, be configured to run at an angle with respect to the length (or a longitudinal axis) of the cast.

Suitable materials for assembling the casting system of the invention are commercially available from WoundKair Concepts, of Fort Worth, Tex., as the TrueKAST™ Total Contact Casting System. A thickness of the outer shell formed by the casting material may typically range from about 1 mm to 4 cm.

An invention has been provided with several advantages. The Total Foot Protection system of the invention has particular applicability to Total Cast Systems, such as those systems used to offload pressure in casting neuropathic and diabetic wounds, but can also be used in casting fractures of the leg or foot. Using the techniques of the present invention, the entire foot is surrounded by a protective pad and therefore there are no areas that will have too much or too little pressure and no area of the foot may rub itself while in the cast. The casting techniques of the invention thus reduce the possibility of errors of the type discussed in the Background of the invention and which reduce the risk of having an ulcer being rubbed on the leg, heel, ankle or toes of the patient. The casting materials of the invention can be applied in one quick application using relatively inexpensive and readily available materials.

While the invention has been shown in several of its forms, it is not thus limited but is susceptible to various changes and modifications without departing from the spirit thereof.

What is claimed is:

1. A method of forming a total contact cast around a foot and leg region of a human patient, the method comprising the steps of:

providing a unitary blank having a top contact surface and an opposite bottom surface and having major and minor generally rectangular planar regions separated by opposing flap regions, the major generally rectangular planar region being sized to receive a plantar surface of the human foot with the minor generally rectangular planar region being sized to receive a hind foot region of the human foot, the opposing flap regions being sized to cover opposing ankle regions of the human foot, the generally rectangular planar regions and flap regions being formed of a pliable foam material so as to be foldable to encompass and envelope the entire foot;

placing the plantar surface of the patient's foot onto the top contact surface of the unitary blank;

folding up the minor generally rectangular planar region of the unitary blank so as to cover the patient's hind foot region;

folding up the opposing ankle regions of the unitary blank to cover the patient's ankle regions;

folding back the major generally rectangular planar region of the unitary blank to cover a top, dorsal region of the foot to thereby form a total foot protection pad;

applying a curable casting material about the foot region of the patient and allowing the casting material to cure to form a hardened cast.

2. The method of claim 1, wherein the pliable foam material is an open-celled polyurethane foam material.

3. The method of claim 2, wherein the top, contact region of the unitary blank has an adhesive applied thereto for restraining the unitary blank about the foot upon folding of the blank.

4. The method of claim 3, wherein the unitary blank is longitudinally dimensioned in a first direction to extend past the foot a sufficient length to be foldable back to provide an overlap region over a dorsal surface of the foot.

5. The method of claim 4, wherein the opposing flap regions of the unitary blank have an outer curvilinear shape defining outwardly extending projections, the projections being positioned and dimensioned to be formed around opposing ankle regions of the foot to form a substantially smooth and pucker free enclosure.

6. The method of claim 5, wherein the unitary blank is provided with a plurality of holes formed therein which communicate the top contact surface and the opposite bottom surface.

7. The method of claim 6, further comprising the steps of placing a strip of pliable pad material down a length of the patient's leg so as to cover that portion of the leg extending upwardly from the top, dorsal region of the foot prior to applying the curable casting material.

\* \* \* \* \*